United States Patent
Butler et al.

(10) Patent No.: US 10,596,325 B2
(45) Date of Patent: Mar. 24, 2020

(54) PEN-TYPE DRUG INJECTION DEVICE WITH IRIS STYLE QUICK COUPLING FOR PISTON ROD RESETTING

(71) Applicant: SANOFI-AVENTIS DEUTSCHLAND GMBH, Frankfurt am Main (DE)

(72) Inventors: Stephen David Butler, London (GB); Mark Philip Horlock, Timperley (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 98 days.

(21) Appl. No.: 15/571,605

(22) PCT Filed: May 9, 2016

(86) PCT No.: PCT/EP2016/060327
§ 371 (c)(1),
(2) Date: Nov. 3, 2017

(87) PCT Pub. No.: WO2016/180774
PCT Pub. Date: Nov. 17, 2016

(65) Prior Publication Data
US 2018/0140779 A1    May 24, 2018

(30) Foreign Application Priority Data
May 8, 2015  (EP) .................................. 15166872

(51) Int. Cl.
*A61M 5/315* (2006.01)
*A61M 5/24* (2006.01)

(52) U.S. Cl.
CPC .......... *A61M 5/31543* (2013.01); *A61M 5/24* (2013.01); *A61M 5/31525* (2013.01);
(Continued)

(58) Field of Classification Search
CPC ................ A61M 5/31543; A61M 5/24; A61M 5/31525; A61M 5/311555; A61M 5/31583; A61M 5/31593
See application file for complete search history.

(56) References Cited

U.S. PATENT DOCUMENTS

| | | | | |
|---|---|---|---|---|
| 4,592,745 A | * | 6/1986 | Rex .......................... | A61M 5/24 604/152 |
| 2013/0204196 A1 | * | 8/2013 | Roberts ............... | A61M 5/3202 604/197 |

FOREIGN PATENT DOCUMENTS

| | | |
|---|---|---|
| EP | 0554995 | 8/1993 |
| WO | WO 98/57688 | 12/1998 |

(Continued)

OTHER PUBLICATIONS

International Search Report and Written Opinion in International Application No. PCT/EP2016/060327, dated Jul. 11, 2016, 11 pages.
(Continued)

*Primary Examiner* — Nathan R Price
*Assistant Examiner* — Melissa A Snyder
(74) *Attorney, Agent, or Firm* — Fish & Richardson P.C.

(57) ABSTRACT

A pen-type drug injection device is disclosed which comprises a housing having a longitudinal axis, a threaded piston rod, a guide member for guiding the piston rod in a drug dispense operation, and a cartridge holder for receiving a cartridge, wherein the cartridge holder is detachable from the housing and wherein the guide member comprises an iris type aperture defined by a plurality of threaded pivotable segments. The drug delivery device is configured such that the aperture increases in diameter when the cartridge holder is being detached from the housing, such that the piston rod is free of the threaded engagement with the guide member and can be reset or pushed back to its initial position, and
(Continued)

decreases in diameter when the cartridge holder is attached, such that the threads on segments reengage the piston rod.

20 Claims, 4 Drawing Sheets

Specification includes a Sequence Listing.

(52) U.S. Cl.
CPC .... *A61M 5/31555* (2013.01); *A61M 5/31583* (2013.01); *A61M 5/31593* (2013.01); *A61M 5/2422* (2013.01); *A61M 2005/2403* (2013.01); *A61M 2005/2407* (2013.01); *A61M 2005/2488* (2013.01)

(56) References Cited

FOREIGN PATENT DOCUMENTS

| WO | WO 03/008023 | 1/2003 |
|---|---|---|
| WO | WO 2012/152667 | 11/2012 |
| WO | WO 2015/018811 | 2/2015 |

OTHER PUBLICATIONS

International Preliminary Report on Patentability in International Application No. PCT/EP2016/060327, dated Nov. 14, 2017, 7 pages.

* cited by examiner

SEQUENCE LISTING

<160> NUMBER OF SEQ ID NOS: 1

<210> SEQ ID NO 1
<211> LENGTH: 39
<212> TYPE: PRT
<213> ORGANISM: Heloderma suspectum

```
<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
            35
```

PEN-TYPE DRUG INJECTION DEVICE WITH IRIS STYLE QUICK COUPLING FOR PISTON ROD RESETTING

CROSS REFERENCE TO RELATED APPLICATIONS

The present application is the national stage entry of International Patent Application No. PCT/EP2016/060327, filed on May 9, 2016, and claims priority to Application No. EP 15166872.0, filed on May 8, 2015, the disclosures of which are expressly incorporated herein in entirety by reference thereto.

TECHNICAL FIELD

The present disclosure relates to a drug delivery device.

BACKGROUND

WO 03/008023 A1 describes a reusable injector pen, wherein after the quantity of medicine contained in a cartridge therein is exhausted by multiple operations of the pen, the cartridge can be removed and replaced by a full cartridge.

SUMMARY

In certain aspects, a drug delivery device providing an improved reset function is provided.

According to an embodiment, a drug delivery device comprises a housing having a longitudinal axis and a piston rod.

The drug delivery device may be an injection device, preferably a pen-type injection device. Preferably, the device is a reusable device such that a cartridge containing a medicament can be exchanged.

The piston rod may have a start position relative to the housing and may be resettable to the start position. For example, the piston rod may be resettable to enable a replacement of a cartridge retaining a medication. Preferably, thereby the drug delivery device is reset such that a first dose of medication from the new cartridge can be dispensed.

The term "piston rod" is used for a component of the drug delivery device which, by carrying out a movement towards the dispensing end of the drug delivery device, causes medicament to be dispensed from the device. In particular, the piston rod may act on a bung or a piston in a medicament container, for example a cartridge, causing medicament to be dispensed from the container. The piston rod may be configured for carrying out a combined axial and rotational movement. As an example, it may be a simple rod or a lead screw having threads for engaging with corresponding parts of the drug delivery device. Preferably, the piston rod comprises at least one threaded section. The piston rod may be of a unitary or a multipart construction.

Furthermore, the drug delivery device may comprise a guide member for guiding the piston rod in a drug dispense operation. Here, the term drug dispense operation may refer to an operation that is activated by a user. During a drug dispense operation a dose of a medication may be delivered out of the drug delivery device. For example, the guide member may comprise a threaded nut threadedly engaged with the piston rod during the drug dispense operation and configured such that it allows the piston rod to advance forward in a distal direction towards the dispensing end of the drug delivery device. The guide member is preferably fixed to the housing, so that, at least during the drug dispense operation, no relative movement between the guide member and the housing occurs.

The drug delivery device further comprises a cartridge holder for receiving a cartridge. Preferably, the cartridge holder may be detachable from the housing and may be configured to be re-attached to the housing after detachment. Advantageously, this allows a replacement of the cartridge arranged in the cartridge holder, e.g. in order to replace an empty cartridge by a full cartridge.

According to an embodiment, the guide member comprises a hole. Preferably, the hole comprises a variable diameter, i.e. the hole is configured such that its diameter may vary during certain operational phases of the device, for example increase or decrease.

Preferably, the guide member is configured such that the piston rod can move through the hole of the guide member during a drug dispense operation. For example, the piston rod may be enabled to advance forward through the hole in a distal direction of the device, i.e. in a direction towards the dispensing end of the drug delivery device during a dose dispense operation.

According to an embodiment, the guide member comprises at least one threaded section. Preferably, the threaded section at least partially confines the hole of the guide member. Furthermore, the threaded section of the guide member may be engageable with the threaded section of the piston rod. For example, the threaded section of the guide member may engage with a threaded section of the piston rod during a drug dispense operation.

The drug delivery device may further comprise a drive member that is configured for transferring a force to the piston rod in a dose dispense operation and, thereby, causing a displacement of the piston rod in a distal direction.

According to an embodiment, the drug delivery device is configured such that the hole increases in diameter when the cartridge holder is being detached from the housing. Preferably, the guide member is moved out of engagement with the piston rod when the cartridge holder is being detached from the housing by an increase of the diameter of the hole of the guide member. In particular, by the increase of the diameter of the hole, a threaded section of the guide member may become disengaged from a threaded section of the piston rod. This may advantageously allow the drug delivery device to be reset by moving the piston rod back to its start position.

According to an embodiment, the drug delivery device is configured such that the hole decreases in diameter when the cartridge holder is being attached to the housing. Thereby, the guide member may be moved into engagement with the piston rod. For example, by the decrease of the diameter of the hole, a threaded section of the guide member may engage with a threaded section of the piston rod, allowing the piston rod to be guided by the guide member during a drug dispense operation.

According to an embodiment, the guide member is configured such that it encircles the piston rod, preferably fully encircles the piston rod. The piston rod is preferably encircled by the guide member at least during a drug dispense operation. Thus, an engagement of the piston rod towards all directions radial to the axis of the piston rod can be achieved allowing a reliable guidance of the piston rod by the guide member. The piston rod may be encircled by the guide member both during a drug dispense operation and during a resetting of the piston rod. In an embodiment, the thread of the guide member does not comprise interruptions. This may be the case at least when the cartridge holder is attached to the housing. Thus, a jamming of the piston rod with the guide member due to an interruption of the thread may be prevented.

According to an embodiment, the guide member comprises a plurality of segments. The segments may be formed as separate members. In particular, the segments may be movable relative to each other. The segments may be arranged along the perimeter of the hole at different angular positions relative to the longitudinal axis of the device. Furthermore, the segments may be located at an offset from each other along the longitudinal axis. The segments may overlap in a projection along the longitudinal axis. Alternatively, the segments may be located at the same axial positions, i.e., without any offset along the longitudinal axis. In this case, the segments may not overlap. Preferably, the segments are directly adjacent to each other such that a jamming of the piston rod may be avoided.

Preferably, the segments are configured such that they move, for example pivot or rotate, when the cartridge holder is being detached and/or attached from the housing of the drug delivery device. As an example, each of the segments may have a pivot point. The pivot point may confine the movement of a segment to a rotational movement around an axis. Preferably, this axis is parallel to a longitudinal axis of the piston rod. During attachment or detachment of the cartridge holder the segments may pivot around the pivot point. As a further example, each of the segments may be movable in a radial direction during detachment and/or attachment of the cartridge holder. As a further example, each of the segments may be enabled to carry out a combined translational and rotational movement. Preferably, the movement of the segments leads to an increase and/or decrease of the diameter of the hole of the guide member.

According to an embodiment, the segments comprise part threads. In particular, each segment may comprise a part thread. When the cartridge holder is attached to the housing and the diameter of the hole is small, the part threads may form the threaded section of the guide member.

According to an embodiment, the segments may be configured to interact with a coupling member of the device. The coupling member may act on the segments such that the segments move, for example pivot. As an example, the segments may comprise engagement members configured to interact with the coupling member. The coupling member may be a part of the cartridge holder or a part coupled to the cartridge holder. The coupling member may be decoupled from the cartridge holder when the cartridge holder is detached from the housing. The coupling member may be configured to remain in the housing when the cartridge holder is detached from the housing.

As an example, the engagement members may comprise protrusions, in particular pins. The coupling member may comprise grooves configured to engage with the protrusions. In particular, the coupling member may be configured as a grooved ring. When the cartridge holder is detached and/or attached from the housing, the grooved ring may rotate. The movement of the segments may be defined by the engagement of the engagement members in the grooves and by the confinement at the pivot points.

As a further example, a part of the drug delivery device may comprise a cammed profile, wherein the guide member is configured to interact with the cammed profile for increasing or decreasing the diameter of the hole. In particular, the coupling member may comprise a cammed profile configured to interact with the segments. The coupling member may be a cammed profile at an inner surface of the cartridge holder, for example. When the cartridge holder is being attached to the housing, projections of the cammed profile may interact with the segments, in particular with an outer surface of the segments, and push the segments radially inwards. Thereby, the diameter of the hole of the guide member may decrease. When the cartridge holder is detached, the segments may move radially outwards due to an elastic force. Alternatively, the coupling member may be configured such that the cammed profile pushes the segments radially outwards during detachment of the cartridge holder. The movement of the segments may be defined by the interaction of the segments with the cammed profile and by the confinement at the pivot points.

According to an embodiment, the drug delivery device is configured such that a detachment operation of the cartridge holder from the housing comprises a rotational movement of the cartridge holder relative to the housing. Preferably, in this case, the hole increases in diameter when the cartridge holder is being rotated for detachment from the housing. For example, by rotating the cartridge holder in order to detach it from the housing, the coupling member engaged with the engagement members of the segments may force the segments to pivot outwards, thereby increasing the diameter of the hole of the guide member. Alternatively, the segments pivot outwards due to an elastic force. As a consequence of the increased diameter, the guide member may become disengaged from the piston rod.

According to an embodiment, the drug delivery device is configured such that an attachment operation of the cartridge holder to the housing comprises a rotational movement of the cartridge holder relative to the housing. Preferably, in this case, the hole decreases in diameter when the cartridge holder is being rotated for attachment to the housing. In particular, by attaching the cartridge holder to the housing, the coupling member may engage or come into contact with the individual segments. Alternatively, during attachment of the cartridge holder, the cartridge holder may engage with the coupling member. The coupling member may be permanently engaged or in contact with the segments. By rotating the cartridge holder in order to attach it to the housing, the segments may be forced to pivot or move inwards, thereby decreasing the diameter of the hole. As a consequence, the guide member may engage with the piston rod, for example by an engagement of threaded sections of the guide member with at least one threaded section of the piston rod.

According to an embodiment, the drug delivery device is configured such that the piston rod is enabled to be moved back in a proximal direction towards its start position after detachment of the cartridge holder. For example, the piston rod may be pushed back or wound back in the proximal direction. After the detachment of the cartridge holder from the housing and the resulting disengagement of the guide member from the piston rod due to the increase of the hole of the guide member, the piston rod may be moved back to its start position thereby resetting the device. In particular, a resetting of the piston rod is unhindered by threaded sections of the guide member and/or the piston rod or any engagements between the two. Once the piston rod is returned to its start position, the cartridge holder may be re-attached to the housing.

Advantageously, the drug delivery device is characterized in that it can be used very intuitively. In addition, very few steps may be required in order to exchange the cartridge of the device. In particular, after detaching the cartridge holder from the housing in order to replace the cartridge of the device, a user may simply need to move back the piston rod and re-attach the cartridge holder containing the new cartridge, without having to take any additional action regarding the disengagement of the piston rod from the guide member. By re-attaching the cartridge holder to the housing of the device, the guide member automatically engages with the piston rod, again without demanding any additional actions of the user of the device. Furthermore, preferably, the resetting of the drug delivery device by pushing back the piston rod after disengagement from the guide member due to the detachment of the cartridge holder may not disturb any other internal parts of the drug delivery device or its mechanism.

The term "medication" or "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO: 1).

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2, or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, refinements and expediencies become apparent from the following description of the exemplary embodiments in connection with the figures.

Like elements, elements of the same kind and identically acting elements may be provided with the same reference numerals in the figures.

DETAILED DESCRIPTION

Figure 1:
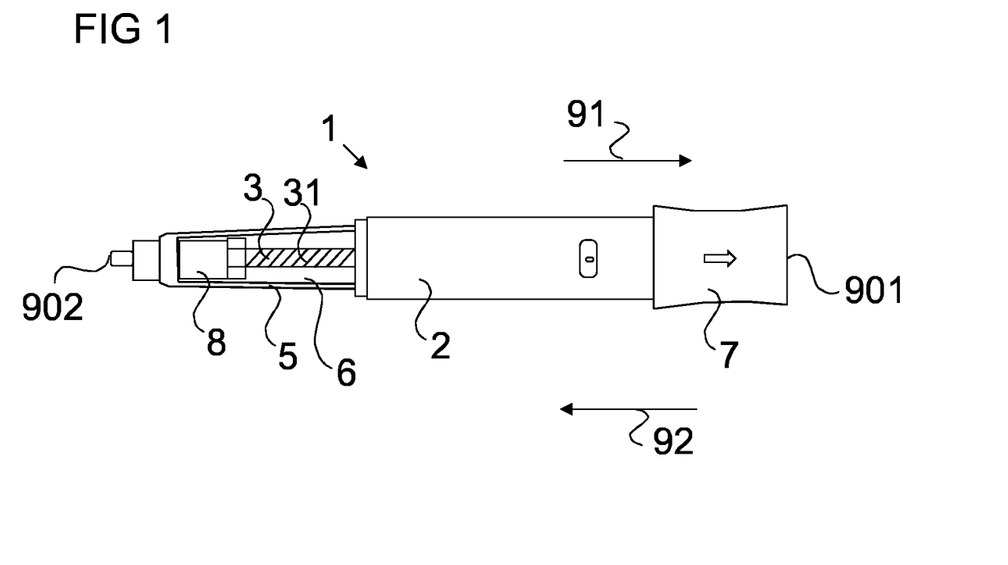
FIG. 1 schematically shows a perspective side view of a drug delivery device.

FIG. 1 shows an embodiment of a drug delivery device 1 which comprises a housing 2 and a cartridge holder 5 which is attached to the housing 2 and which is detachable from the housing 2. Preferably the cartridge holder 5 is suited for holding a cartridge 6 which may contain a medication. The housing 2, the cartridge holder 5 and/or the cartridge 6 may have a tubular shape. The drug delivery device 1 comprises a dose button 7 for setting and dispensing a dose of a medication. The drug delivery device 1 may be a pull-push device such that the dose button 7 is pulled out of the housing 2 for setting a dose and is pushed towards the housing 2 for dispensing a dose.

The medication retained in the cartridge 6 is preferably liquid medication. The cartridge 6 preferably comprises a plurality of doses of the medication. The medication may comprise insulin, heparin, or growth hormones, for example. The cartridge 6 has an outlet at its distal end. Medication can be dispensed from the cartridge through its outlet. The device 1 may be a pen-type device, in particular a pen-type injector. The device 1 may be or a reusable device. The device 1 may be a device configured to dispense fixed doses of the medication or variable, preferably user-settable, doses. The device 1 may be a needle-based or a needle free device. The device 1 may be an injection device.

The term "distal end" of the medication delivery device 1 or a component thereof may refer to that end of the device or the component which is closest to the dispensing end of the device 1. The term "proximal end" of the medication delivery device 1 or a component thereof may refer to that end of the device or the component which is furthest away from the dispensing end of the device. In FIG. 1, the distal end of the device 1 is assigned reference numeral 902 and the proximal end of the device is assigned reference numeral 901. The arrows 91 and 92 are used to indicate the proximal and the distal direction, i.e. the direction towards the proximal end 901 and towards the distal end 902.

A piston 8 is retained within the cartridge 6. The piston 8 is movable with respect to the cartridge 6. The piston 8 may seal the medication within the cartridge 6. The piston 8 expediently seals the interior of the cartridge 6 proximally. Movement of the piston 8 with respect to the cartridge 6 in the distal direction causes medication to be dispensed from the cartridge 6 through its outlet during operation of the device 1.

The drug delivery device 1 further comprises a piston rod 3. The piston rod 3 may be configured for transferring force to the piston 8, thereby displacing the piston in the distal direction 92 with respect to the cartridge 6. A distal end face of the piston rod 3 may be arranged to abut a proximal end face of the piston 8.

The drug delivery device 1 may comprise a drive member (not shown in this figure) for transferring a force from the dose button 7 to the piston rod 3 and, thereby, causing a displacement of the piston rod 3 in a dose dispense operation. Furthermore, the drug delivery device 1 may comprise a guide member (not shown in this figure) for guiding the piston rod 3 in a dose dispense operation. In particular, the piston rod 3 comprises a threaded section 31 in engagement with the guide member. The piston rod 3 may be configured as a lead-screw. During a dose dispense operation, the piston rod 3 may be screwed through the guide member, i.e. may carry out a helical movement.

The piston rod 3 may be flexible or not. It may have a circular or non-circular cross-section. It may be made of any suitable material known by a person skilled in the art and may be of unitary or multipart construction.

The drug delivery device 1 may be a manually, in particular non-electrically, driven device.

Figure 2:
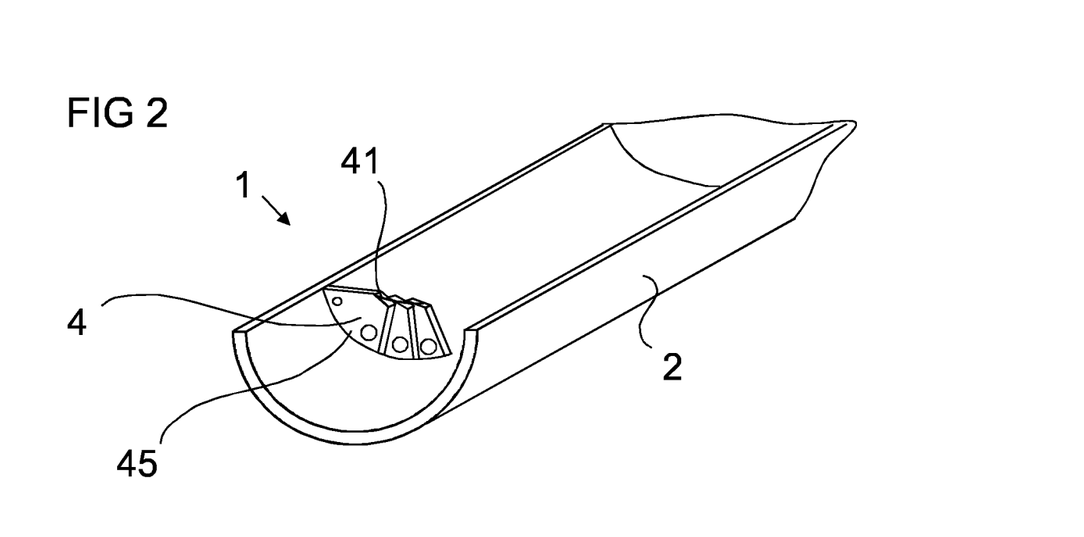
FIG. 2 schematically shows a perspective sectional view of a part of the drug delivery device of FIG. 1.

FIG. 2 schematically shows a perspective sectional view of a part of the housing 2 of the drug delivery device 1 of FIG. 1. The drug delivery device 1 comprises a guide member 4 which is fixed to the housing 2 during dose dispense operations such that a relative movement of the guide member 4 and the housing 2 is prevented. The guide member 4 may be directly fixed to the housing 2 of the device 1 or may be fixed to an insert fixed to the housing 2 of the device 1. Furthermore, when the cartridge holder 5 is attached to the housing 2, the guide member 4 may be coupled with the cartridge holder 5. Alternatively, the guide member 4 may be fixed to a cartridge holder 5 or may be a part of the cartridge holder 5. The guide member 4 is configured to guide the piston rod 3 in a drug dispense operation.

Figure 3A:
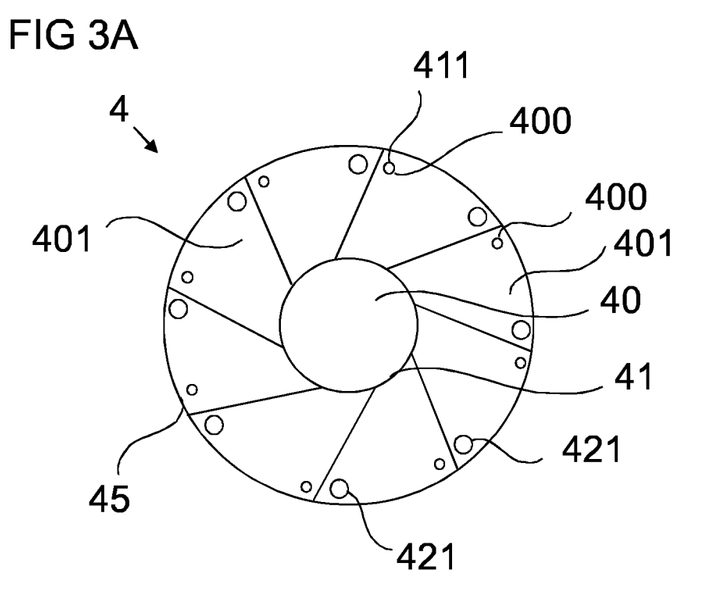
FIGS. 3A and 3B schematically show a detailed view of a guide member.
Figure 3B:
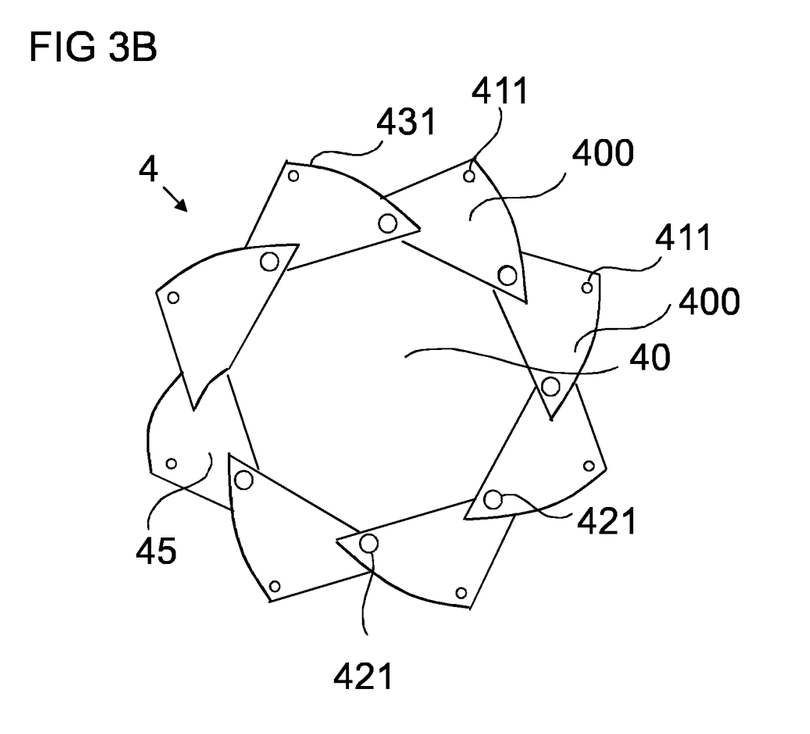

FIGS. 3A and 3B show detailed views of the guide member 4. The guide member 4 of FIG. 2 is depicted in more detail in FIGS. 3A and 3B. FIG. 3A shows the guide member 4 in a state where the cartridge holder 5 is attached to the housing 2. FIG. 3B shows the guide member 4 in a state where the cartridge holder 5 is detached from the housing 2.

The guide member 4 comprises a hole 40 having a variable diameter. In particular, the diameter of the hole 40 may increase or decrease during detachment or attachment of the cartridge holder 5 to the housing 2.

Furthermore, the guide member 4 comprises a threaded section 41. In particular, the threaded section 41 is formed in a region of the perimeter of the hole 40 and is configured such that it may engage with the threaded 31 section of the piston rod 31.

The guide member 4 is formed by a plurality of segments 401, wherein each segment 401 adjoins to two other segments 401. Each of the segments 401 comprises a part thread. The part threads form the threaded section 41 of the guide member 4. The segments 401 may be located at an axial offset from each other, in particular may have an offset relative to a longitudinal axis of the device 1 (see FIG. 2). The segments 401 comprise engagement members 400 that are configured to interact with a coupling member (see FIG. 4). The engagement members 400 may comprise protrusions 411, for example pins.

Furthermore, each segment 401 comprises a pivot point 421. The segments 401 are configured such that they pivot or rotate around the pivot points 421 when the cartridge holder 5 is detached or attached to the housing 2. Preferably, the pivot points 421 are configured such that the segments 401 pivot or rotate around an axis that is parallel to a longitudinal axis of the housing 2.

Figure 4:
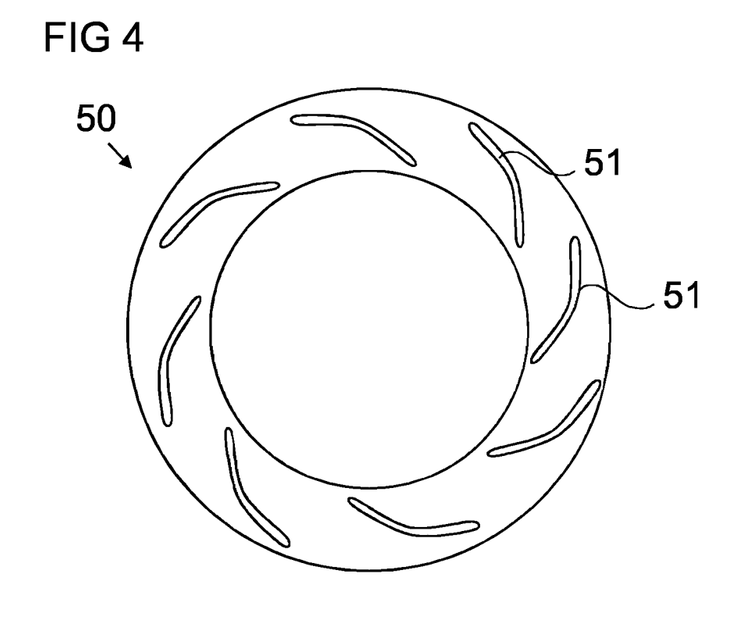
FIG. 4 schematically shows a coupling member.

FIG. 4 shows an embodiment of a coupling member 50. The coupling member 50 may be a part of the cartridge holder 5, may be permanently coupled with the cartridge holder 5 or may remain in the housing 2 of the device 1 when the cartridge holder 5 is detached. When the cartridge holder 5 is attached to the housing, the cartridge holder 5 is coupled with the coupling member 50 such that a rotation of the cartridge holder 5 causes a rotation of the coupling member 50. As an example, the coupling member 50 may comprise a protrusion, for example a pin, which may engage with the cartridge holder 5 during attachment of the cartridge holder 5.

The coupling member 50 is configured as a grooved ring. In particular, the coupling member 50 comprises grooves for engagement with the engagement members 400.

When the coupling member 50 is rotated during attachment or detachment of the cartridge holder 5, a movement of the engagement members 400 and, thereby, the individual segments 401, is guided by the grooves 51. Thereby, the segments 401 pivot inwards or outwards. This leads to a decrease or increase of the diameter of the hole 40. The mechanism of the guide member 4 may correspond to the mechanism of an iris in a camera. The guide member may correspond to a shutter.

During a removal of the cartridge holder 5, in particular by rotating the cartridge holder 5 for detachment, the coupling of the cartridge holder 5 with the engagement members 400 of the segments 401 force the segments 401 to pivot outwards, causing the threaded hole 40 to increase in diameter. Consequently, the diameter of the hole 40 becomes larger than the outer diameter of the piston rod 3, allowing the piston rod 3 to be pushed back into the housing to its starting position, unhindered by the threaded sections 41 of the hole and by the threaded sections of the piston rod 3 or any engagement between these parts.

Advantageously, the drug delivery device 1 is configured for a very small reset force, i.e. the piston rod 3 can easily be pushed back to its starting position.

In a further embodiment, the coupling member 50 may be configured as a camming member. The camming member may be coupled with the cartridge holder 5 or may be part of the cartridge holder 5. The camming member may comprise a cammed profile, in particular cammed surfaces for interaction with surfaces of the guide member 4. As an example, the camming member may have the shape of a sleeve enclosing the guide member 4. The cammed surface may comprise protrusions. When a cartridge holder 5 is attached to the housing, 2, the camming member may rotate such that the protrusions act on outer surfaces 431 (see FIG. 3B) of the segments 401 such that the segments 41 are caused to pivot around the pivot points 421. In this case, the segments 41 may not comprise the pin-shaped engagement members 411. Thereby, the diameter of the threaded hole 40 decreases and the guide member 4 is engaged with the piston rod 3. The guide member 4 may be elastically biased such that when the cartridge holder 5 is detached from the housing 2 and the cammed surface does not force the segments 401 inwards, the segments 401 may deflect outwards, whereby the diameter of the hole 40 increases again.

FIGS. 5A to 5D schematically show perspective side views of the drug delivery device 1 of FIG. 1 at different stages of the resetting of the device 1.

Figure 5A:
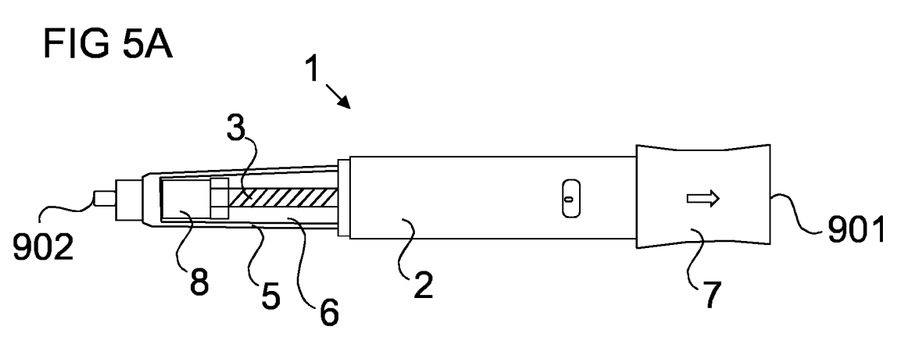
FIGS. 5A to 5D schematically show perspective side views of the drug delivery device of FIG. 1 at different stages of the resetting of the device.

In FIG. 5A, the cartridge holder 5 is attached to the housing 2 of the drug delivery device 1. As described in connection with the FIGS. 2 to 3B, the guide member 4 forms a threaded nut engaged with the piston rod 3, thereby guiding the piston rod 3 in a dose dispense operation.

Figure 5B:
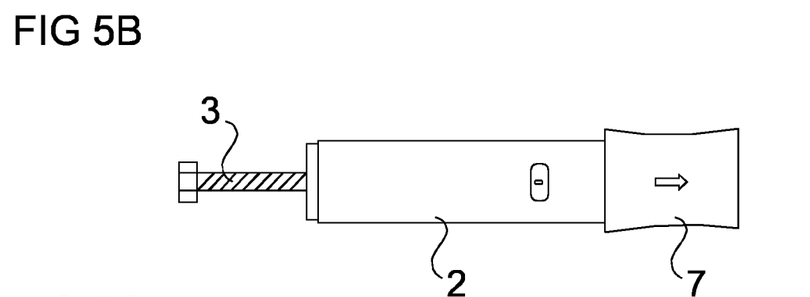

FIG. 5B shows the device 1 after detachment of the cartridge holder 5. The segments 401 of the guide member 4 have been pivoted outwards and have been disengaged from the piston rod 3 so that the piston rod 3 can be pushed back in the proximal direction 91 up to its start position unhindered by the threaded sections 41 of the hole 40 or by the threaded sections of the piston rod 3.

Figure 5C:
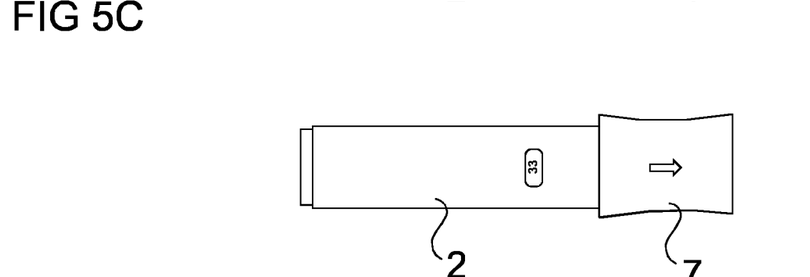

FIG. 5C shows the drug delivery device 1 after the piston rod 3 has been pushed back to its start position.

Figure 5D:
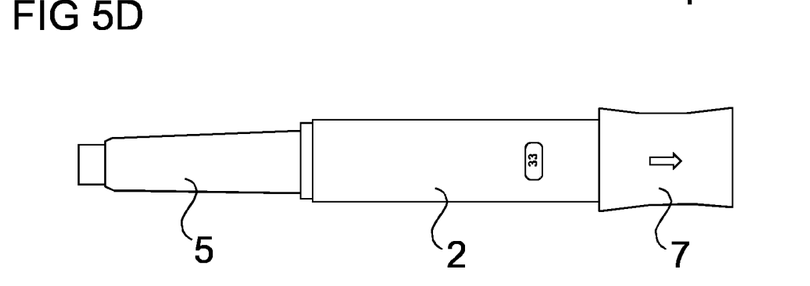

Finally, as shown in FIG. 5D, the cartridge 6 can be replaced and the cartridge holder 5 can be re-attached to the housing 2, thereby decreasing the diameter of the threaded hole such that the guide member 4 is re-engaged with the piston rod 3.

The invention is not restricted by the description on the basis of the exemplary embodiments. Rather, the invention encompasses any new feature and also any combination of features, which in particular comprises any combination of features in the patent claims, even if this feature or this combination itself is not explicitly specified in the patent claims or exemplary embodiments.

REFERENCE NUMERALS 1 drug delivery device
2 housing
3 piston rod
31 threaded section
4 guide member
40 hole
41 threaded section
45 shutter
400 engagement members
401 segment
411 protrusion
421 pivot point
431 outer surface
5 cartridge holder
50 coupling member
51 groove
6 cartridge
7 dose button
8 piston
91 proximal direction
92 distal direction
901 proximal end
902 distal end

The invention claimed is:

1. A drug delivery device comprising:
 a housing having a longitudinal axis;
 a piston rod;
 a guide member for guiding the piston rod in a drug dispense operation; and
 a cartridge holder for receiving a cartridge,
 wherein the cartridge holder is detachable from the housing,
 wherein the guide member comprises a hole with a variable diameter,
 wherein the guide member comprises a plurality of segments,
 wherein the segments are configured to pivot when the cartridge holder is being detached or attached to the housing, and
 wherein the drug delivery device is configured such that the hole increases in diameter when the cartridge holder is being detached from the housing.

2. The drug delivery device according to claim 1, wherein the piston rod comprises a threaded section.

3. The drug delivery device according to claim 1, wherein the guide member comprises at least one threaded section engageable with the piston rod.

4. The drug delivery device according to claim 1, wherein the guide member is configured such that it encircles the piston rod at least during the drug dispense operation.

5. The drug delivery device according to claim 1, wherein the segments are axially offset from each other.

6. The drug delivery device according to claim 1, wherein the segments are configured to pivot around an axis parallel to the longitudinal axis of housing.

7. The drug delivery device according to claim 1, comprising a coupling member configured to interact with the segments for increasing or decreasing the diameter of the hole.

8. The drug delivery device according to claim 7, wherein the segments comprise protrusions to engage with the coupling member.

9. The drug delivery device according to claim 7, wherein the coupling member comprises a cammed profile.

10. The drug delivery device according to claim 1, wherein:
 the cartridge holder is configured to be detached from the housing through a rotational movement of the cartridge holder relative to the housing, and
 the hole is configured to increase in diameter when the cartridge holder is being rotated for detachment.

11. The drug delivery device according to claim 1, wherein:
 the cartridge is configured to be attached to the housing through a rotational movement of the cartridge holder relative to the housing,
 the hole is configured to decrease in diameter when the cartridge holder is being rotated for attachment.

12. The drug delivery device according to claim 1, wherein the piston rod is movable in a proximal direction towards a start position after detachment of the cartridge holder.

13. The drug delivery device according to claim 1, wherein the drug delivery device is a pen-type injection device.

14. The drug delivery device according to claim 1, further comprising the cartridge, wherein the cartridge contains a medicament.

15. A method of operating a drug delivery device, the method comprising:
 detaching a cartridge holder of the drug delivery device from a housing of the drug delivery device, thereby enlarging a hole of a guide member of the drug delivery device;
 mounting a cartridge to the cartridge holder;
 attaching the cartridge holder to the drug delivery device; and
 initiating a drug dispense operation in which the guide member of the drug delivery device guides a piston rod of the drug delivery device to displace a piston in the cartridge distally relative to the cartridge.

16. The method of claim 15, wherein detaching the cartridge holder of the drug delivery device comprises causing the hole of the guide member to enlarge and to disengage from the piston rod.

17. The method of claim 15, further comprising moving the piston rod proximally relative to the housing of the drug delivery device while the cartridge holder is detached from the housing of the drug delivery device and while the hole of the guide member is disengaged from the piston rod.

18. The method of claim 15, wherein attaching the cartridge holder to the drug delivery device comprises causing the hole of the guide member to decrease in size and to engage with the piston rod.

19. The method of claim 15, wherein detaching the cartridge holder comprises rotating the cartridge holder relative to the housing, thereby causing segments of the guide member defining the hole to pivot outward to enlarge the hole.

20. A drug delivery device comprising:
 a housing having a longitudinal axis;
 a piston rod;
 a guide member for guiding the piston rod in a drug dispense operation, the guide member comprising a plurality of segments and a hole with a variable diameter;
 a coupling member configured to interact with the segments for increasing or decreasing the diameter of the hole; and a cartridge holder for receiving a cartridge,
wherein the cartridge holder is detachable from the housing, and
wherein the drug delivery device is configured such that the hole increases in diameter when the cartridge holder is being detached from the housing.

\* \* \* \* \*